(12) United States Patent
Hager et al.

(10) Patent No.: US 6,509,496 B1
(45) Date of Patent: Jan. 21, 2003

(54) PROCESS FOR MAKING MINERAL, FOOD OR PHARMACEUTICAL GRADE SALT PRODUCTS

(75) Inventors: Dennis M. Hager, Bountiful, UT (US); William E. Stern, Provo, UT (US); Kim R. Nielsen, Layton, UT (US)

(73) Assignee: Nutrapure, Inc., Ogden, UT (US)

( * ) Notice: Subject to any disclaimer, the term of this patent is extended or adjusted under 35 U.S.C. 154(b) by 37 days.

(21) Appl. No.: 09/691,055

(22) Filed: Oct. 19, 2000

(51) Int. Cl.[7] .............................................. C07C 229/00
(52) U.S. Cl. ........................ 562/445; 562/587; 562/590
(58) Field of Search ................................. 562/587, 590, 562/445

(56) References Cited

U.S. PATENT DOCUMENTS

| | | | |
|---|---|---|---|
| RE3,395 E | 4/1869 | Smith | |
| 2,396,115 A | 3/1946 | Nicholls | |
| 3,821,224 A | 6/1974 | Braeuer et al. | |
| 3,862,219 A | 1/1975 | Lindsay et al. | |
| 3,978,245 A | 8/1976 | Deininger et al. | |
| 4,013,773 A | 3/1977 | Murakami et al. | |
| 4,214,996 A | 7/1980 | Buddemeyer et al. | |
| 4,251,449 A | 2/1981 | Schreur | |
| 4,315,927 A | 2/1982 | Evans | |
| 4,391,837 A | 7/1983 | Kocher | |
| 4,684,528 A | 8/1987 | Godfrey | |
| 4,700,000 A | 10/1987 | Merkel et al. | |
| 4,740,380 A | 4/1988 | Melachouris et al. | |
| 4,814,177 A | 3/1989 | Walsdorf et al. | |
| 4,836,994 A | 6/1989 | Inoue et al. | |
| 4,855,494 A | 8/1989 | Margureanu et al. | |
| 4,867,942 A | 9/1989 | Gergely et al. | |
| 4,882,161 A | 11/1989 | Scheurer et al. | |
| 4,883,683 A | 11/1989 | Sano et al. | |
| 4,985,593 A | 1/1991 | Walsdorf et al. | |
| 5,073,380 A | 12/1991 | Babu et al. | |
| 5,077,310 A | 12/1991 | Yamashita et al. | |
| 5,089,276 A | 2/1992 | Yamashita et al. | |
| 5,186,965 A | 2/1993 | Fox et al. | |
| 5,208,372 A | 5/1993 | Vidal et al. | |
| 5,227,007 A | 7/1993 | Tateba et al. | |
| 5,231,225 A | 7/1993 | Baniel et al. | |
| 5,389,387 A | 2/1995 | Zuniga et al. | |
| 5,922,351 A | 7/1999 | Daher | |

FOREIGN PATENT DOCUMENTS

GB          1030711          5/1966

*Primary Examiner*—Paul J. Killos
(74) *Attorney, Agent, or Firm*—Banner & Witcoff, Ltd.

(57) ABSTRACT

A process for forming a mineral, food or pharmaceutical grade salt product is described. The process comprises completing all the process steps in a single reactor vessel resulting in high yield and purity in shortened processing times on the order of 1/10 to 1/3 of the processing times required in prior processes.

29 Claims, 6 Drawing Sheets

PROCESS FOR MAKING MINERAL, FOOD OR PHARMACEUTICAL GRADE SALT PRODUCTS

FIELD OF THE INVENTION

The present invention is directed to a process for making a number of mineral, food or pharmaceutical grade salt products. The process is most preferably designed to achieve complete or nearly complete reaction of all reactants, resulting in high yield and purity in a shortened processing time to arrive at the desired final product having the sought after moisture content. Typically, a variety of salts are thus mass produced with reduced processing time and cost.

BACKGROUND OF THE INVENTION

Unduly lengthy batch processes have been utilized to form a variety of mineral, food or pharmaceutical grade salt products such as calcium citrate, calcium malate, zinc citrate, magnesium citrate, and the like. Previously used processes for making the aforementioned products involve various steps. These steps, in general, are as follows: (1) mixing the reactants, sometimes with water, at ambient temperature (typically, about 25° C. at 1 atmosphere pressure); (2) adding water to the mixed reactants, if not done in (1) above, at ambient temperature; (3) mixing the ingredients sometimes with heating to initiate reaction of the reactants; (4) after reaction has taken place, removing the so-heated product including any unreacted reactants from the reactor vessel; and (5) drying the product to the desired moisture content outside the reactor vessel.

Additionally, the previously used processes required extended drying times, typically outside the reactor vessel for achieving the desired moisture content within the mineral, food or pharmaceutical grade salt product. For example, using previously used processes to form the desired mineral, food or pharmaceutical grade salt product having the desired moisture content (typically from about 2% to about 6% moisture content) required a too long drying cycle, sometimes on the order of 1–5 days for product batches on the order of about 100 kg in size. Without being bound by theory, Applicants now believe that the long drying times are due to the addition of water in an amount thought to be necessary with the prior processes. Further, oftentimes the water and associated moisture content cause the formation of "large cakes." These "cakes" are required to be broken down and/or ground to manageable size granules to facilitate drying and to facilitate forming salt products having the desired moisture content. As a result, unfortunately, the overall cost, time, and process complexity for forming the desired salt products are disadvantageously increased.

Previously, the salt products were made in several steps, including conducting most of the drying of the salt products outside the reactor vessel, to accommodate the lengthier drying times. The disadvantages of having long drying times include, but are not limited to, requiring separate drying chambers or (in some cases) drying rooms, accommodating longer production times, and increasing costs of production. As a result, with prior processes, increased storage, processing space and processing time had to be allocated.

All of these factors contribute to increased production costs and decreased flexibility of using the processing equipment for switching from one salt product to another. Thus, for example, if one wanted to switch the product line from zinc citrate to calcium citrate, the longer processing times would delay the switch over because the drying chambers would be occupied with as yet undried product. One had to wait until the product was sufficiently dried before the drying chamber could be vacated for drying the next product in the same chamber. Alternatively, a separate drying chamber was needed if both products were to be dried simultaneously. The cost of such measures can be nearly or altogether eliminated using the presently claimed inventive process which utilizes less water than previously thought necessary.

Until now, for comparable batch sizes (e.g., about 100 kg batches) nearly complete reaction of the starting reactants with the desired purity and yield was not achieved while obtaining the desired shortened processing time goals, typically on the order of from about 1 to about 9 hours, preferably from about 1 to about 6 hours, more preferably from about 1 to about 2 hours, even more preferably about 1 hour, and most preferably about ½–1 hour or less. The desired purity level of mineral, food or pharmaceutical grade salt products is that which is suitable for the intended use of the same, e.g. as a mineral, as a food ingredient, or as a pharmaceutical ingredient. For mineral, food or pharmaceutical grade salt products, the desired purity will often be that specified in the *United States Pharmacopeia*, 21st Edition, 1985 (or its later editions), in *Remington's Pharmaceutical Sciences*, 16th Edition, Mack Publishing Co., Easton, Pa., 1980 (or its later editions), or in the *Handbook of Chemistry and Physics*, 57th Edition, CRC Press, Cleveland, Ohio, 1977 (or its later editions). For food grade salt products, the purity level may often be lower than that specified for pharmaceutical grade salt products.

The desired yield (actual/theoretical×100=% yield) for mineral, food or pharmaceutical grade salt products is on the order of from about 90% to about 100%, preferably from about 95% to about 100%, more preferably from about 96% to about 100% and most preferably from about 98% to about 100% or 98%–100%.

It is desirable to provide a process for making mineral, food or pharmaceutical grade salt products in a single reactor vessel (including completing or nearly completing the drying step) wherein the yield and purity are high and the processing time is substantially shortened. It also is desirable to provide a process wherein the drying step of the process is short enough that it can be completed in the reactor vessel itself (preferably, from the start of the process—mixing the dry reactants—to its finish—forming the desired product to at least the desired product moisture content and optionally meeting any other product specifications) in a relatively short processing time (e.g., preferably, on the order of 1–6 hours, more preferably 1–2 hours, even more preferably 1 hour, and most preferably ½–1 hour or less as opposed to 1–5 days for comparable batch sizes from about 50 kg to about 600 kg) without having to resort to the use of a separate drying chamber.

It also is desirable to provide a process for making mineral, food or pharmaceutical grade salt products in a single reactor vessel wherein the yield is on the order of 95–100%, the purity level satisfies the product specification, the processing time is on the order of about 1–2 hours and the drying, sufficient to satisfy the product specification (e.g., about 6% by weight or less moisture content), also can be completed in the reactor vessel itself within the 1–2 hours processing time. Alternatively, it is desirable to provide the aforementioned process except that the drying is conducted in a drying vessel or drying chamber other than reactor vessel itself; however, the total processing time including the drying time is still completed within the 1–2 hours processing time for a 20–600 kg (e.g., 50 kg, 100 kg or 150 kg batch) batch of dry or essentially dry necessary reactants. Necessary reactants are those required to form the desired product.

SUMMARY OF THE INVENTION

It is thus an object of the present invention to provide a process for making mineral, food or pharmaceutical grade salt products wherein a high purity level and yield are achieved and the final product is formed with the desired moisture content (e.g. by completing or substantially completing the drying in the reactor vessel itself) in a substantially shortened processing time for comparable yields and purity over those achieved with prior processes. It is desirable to provide such a process for the cost savings and for the other associated advantages which will be readily apparent to one of ordinary skill based on the disclosure of this patent application.

It is yet another object of the present invention to provide the aforementioned process to reduce the processing time for example, from about 1–5 days down to preferably about 1–6 hours, more preferably about 1–2 hours, even more preferably about 1 hour, and most preferably about ½–1 hour or less, and thereby reduce the costs and inconveniences associated with such process (for comparable batch sizes such as 100 kg, with comparable or better yield and purity).

These and other advantages are achieved by the inventive process noted below. According to one embodiment of the inventive process, the process for forming a mineral, food or pharmaceutical grade salt product comprises the steps of:

(a) loading or providing reactants necessary for making the mineral, food or pharmaceutical grade salt product in a reactor vessel;

(b) with optional mixing, adjusting the temperature of the reactants to a first set point temperature in the reactor vessel, wherein the first set point temperature is above about 25° C. when operating the process at about 1 atmosphere pressure;

(c) with optional mixing, adding a fluid to the reactants of step (b) at a rate and in an amount sufficient to initiate reaction of all or nearly all of the reactants to form a first mixture; and (d) with optional mixing, adjusting the temperature of the first mixture to a second set point temperature for a time sufficient to evaporate substantially all of the fluid to yield the mineral, food or pharmaceutical grade salt product having a desired moisture content. According to another embodiment, the "mixing" in any of steps (b), (c) and/or (d) may be intermittent or continuous. Further, according to still another embodiment, the desired moisture level is dictated by the product specification and is typically less than about 10–12%, preferably less than about 7%, more preferably less than about 6%, even more preferably from about 1 to about 6% and most preferably from about 1% to about 4%.

BRIEF DESCRIPTION OF THE DRAWINGS

The above-noted FIGS. 2 and 3 are not drawn to scale.

DETAILED DESCRIPTION OF THE INVENTION

Figure 1A:
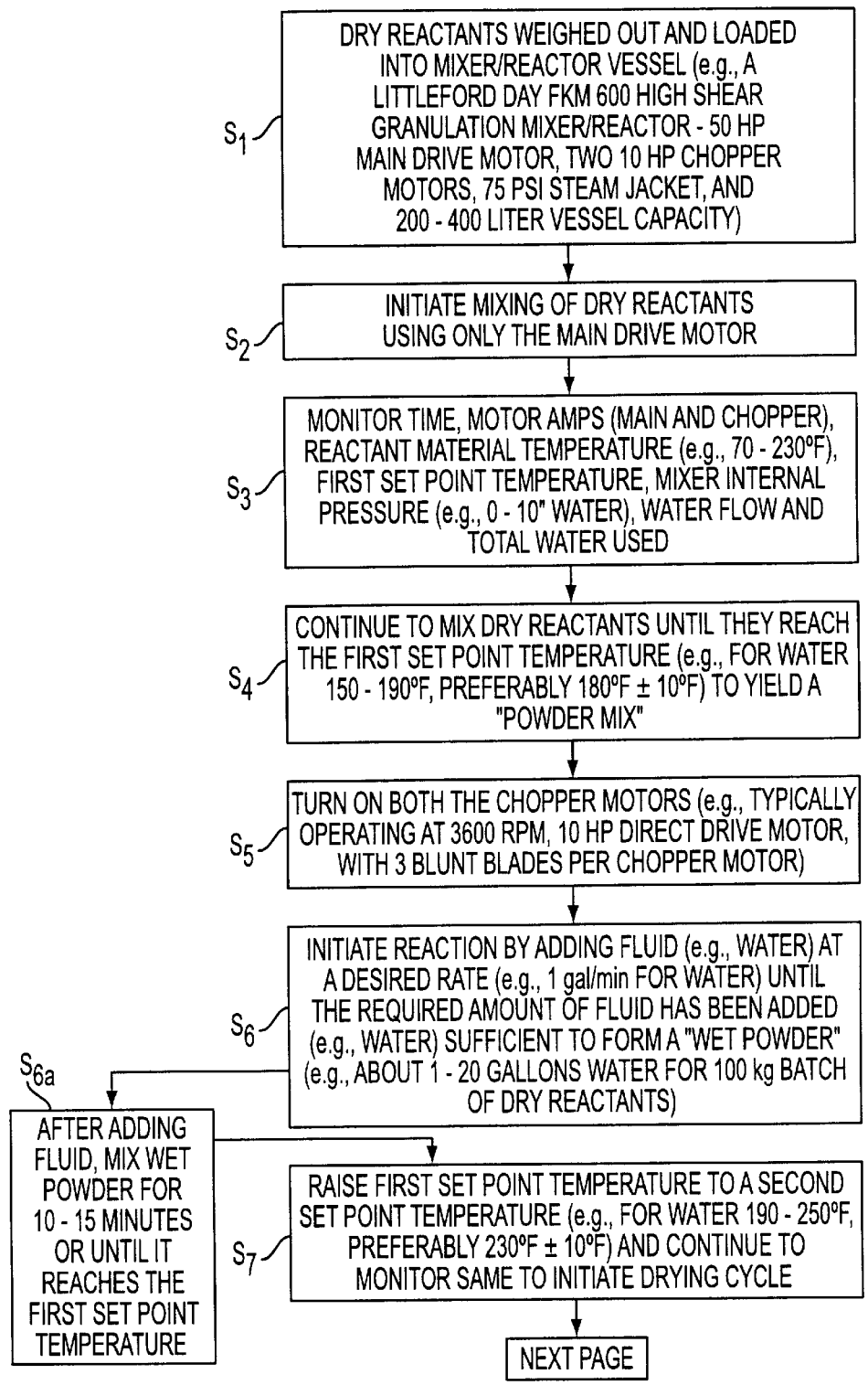
FIGS. 1a–1c represent a flow-chart of an exemplary process in accordance with the present invention outlining various process steps.

Unless indicated otherwise, all percentages are percentages by weight based on a total weight of the final salt product. All references cited herein are incorporated by reference in their entirety. Further, the terms "moisture level" or "moisture content" are used synonymously and refer to non-hydrated water molecules (e.g., not waters of hydration such as those found in salt hydrates) associated with the salt product.

The presently claimed process may be carried out in a suitable reactor such as a Littleford reactor. Though the present invention is described in conjunction with the reactor vessel depicted in FIGS. 2 and 3 (which reactor vessel is a schematic representation of a Littleford Day reactor vessel), it is understood that any reactor vessel that provides adequate heating, temperature control, product inlet and outlet ports, fluid inlet ports and sufficient mixing may be used. Further, the exact positions of the various parts may be altered provided that the so-altered configuration functions in about the same manner as the exemplary reactor of FIG. 2. For example, though not so depicted in FIG. 2, inlet port 10a and outlet port 10b maybe disposed on steam jacket 10 to be in opposing orientation to each other, i.e., for a cylindrical reactor vessel such as 1, if inlet port(s) 10a (may be more than one) is/are located near the top of the vessel, then outlet port(s) 10b (may be more than one) is/are near the bottom of the vessel.

Referring to FIGS. 1a–1c and FIGS. 2–3, according to one embodiment of the present invention, dry reactants (not shown) are weighed out and loaded into the central chamber 30 of reactor vessel 1 via inlet port 80. Preferably, the dry reactants are weighed out in and loaded in about stoichiometric quantities. By use of the term "stoichiometric quantity" or "stoichiometric amount" it will be understood that a sufficient amount of each reactant necessary to complete reaction with all or substantially all of the other reactant(s) is provided to form the desired product. While the present inventive process may be carried out with non-stoichiometric amounts of one or more reactants, it is preferred to provide stoichiometric amounts of all of the reactants needed to form a desired food grade or pharmaceutical grade salt product.

During loading, exemplary port 90 is kept closed by maintaining port door 90a closed, thus preventing loss of reactants during loading and further processing. Within chamber 30 is a central shaft 40 disposed about central axis 40a. To shaft 40 are connected mixing plows 50 via shafts 50a. It should be noted that while multiple mixing plows are described, a single plow or multiple plows may be provided within chamber 30. Preferably, plows 50 have a wedge shape (with each side of the wedge being either flat, convex, concave or a combination thereof), which wedge shape is well known to those of ordinary skill experienced with using Littleford Day-type reactor vessels. Central shaft 40 is connected to a main drive motor 20. Preferably, the main drive motor 20 has sufficient horse power to adequately mix the batch size of reactants loaded into chamber 30 permitting relatively uninhibited and smooth rotation of shaft 40 either in the clockwise or counterclockwise direction. Preferably, the rotation of shaft 40 is in the direction that causes the leading tapered edge 50b of all the wedge shaped plows 50 to push through the reactants loaded into chamber 30 during rotation of shaft 40 by motor 20. To accomplish the same, the plows 50 should preferably have all the leading edges 50b oriented in the same direction as the direction in which the shaft 40 is to be rotated when motor 20 is engaged. While the aforementioned description refers to plows 50, it is understood that any other equivalent mixing element (e.g., scoop, heat transfer blade, other blades, fingers, forks, etc.) may be used.

The reactor vessel 1 is equipped with an exemplary steam jacket 10 disposed around the outer circumference of chamber 30. The steam jacket 10 is connected to an inlet steam tube 10a and an outlet steam tube 10b. The inlet steam tube 10a is connected to a pressure valve 10c. The steam jacket 10 is connected to a temperature controller (not shown) and a temperature monitor in chamber 30 (not shown) sufficient to control the temperature inside the chamber 30 and its contents. While the heating of chamber 30 is accomplished by use of a steam jacket, any other equivalent "heating element" may be used in place of the steam jacket 10. An example of another "heating element" may be a hot oil jacket (with oil or other suitable fluid flowing through jacket or maintained therein) or an electric blanket of adequate size and power to accomplish the required heating and the like.

Once the reactants are placed in chamber 30, door 90a is closed, and the steam jacket is set to the first set point temperature typically from about 150° F. to about 190° F., preferably from about 155° F. to about 189° F., more preferably from about 160° F. to about 188° F., even more preferably from about 165 to about 185° F. and most preferably about 180° F. Other exemplary first set point temperatures include 150° F., 155° F., 160° F., 165° F., 170° F., 175° F., 180° F., 185° F., and 190° F. The first and second set point temperatures disclosed herein are those appropriate for operation of the claimed process when operated at ambient pressure (e.g., 1 atmosphere). However, if the process is operated at lower than atmospheric pressure, the cycle time will be reduced optionally together with the first and/or second set point temperatures as would be readily understood by one of ordinary skill. The converse is also true. The first set point temperature adjusts the heat from the steam jacket such that the temperature of the contents of chamber 30 reach the first set point temperature. With the first set point temperature being set, the reactants in chamber 30 are mixed either with the plows 50 alone rotating about shaft 40 via motor 20 or with the aid of chopper blades 60a attached to choppers 60 and a chopper motor (not shown). Though not preferred, chopper blades 60a may sometimes be used alone. Typically, the shaft of chopper 60 is equipped with one or more chopper blades 60a, preferably three. Each chopper blade is preferably flat and in the shape of an "X" or "+". However, any suitable shape and number of chopper blades may be used to mix the reactants in the chamber 30. Further, the choppers are preferably used to "de-lump" the material within chamber 30 sufficient to avoid a separate "de-lumping" and/or drying step at the end of the claimed process. Such use of choppers 60 during the claimed process permits the final mineral, food or pharmaceutical grade salt product so made to be formed in a "de-lumped" formulation, which is directly amenable to a further grinding operation if necessary to satisfy a desired particle size distribution. By this inventive process, an intervening "de-lumping" step is avoided. Please note that the term "de-lump" is a term of art well understood by one of ordinary skill in the relevant art.

The term "de-lump" means to reduce moist, semi-moist or dry solids down to grain size. See, for example, the brochure for DYNAMIC AIR TUFFER Aerator/Lump Breaker Series 329, incorporated herein by reference in its entirety.

Preferably, the main drive motor 20 is a 50 horse power motor and each of the choppers 60 are equipped with a 10 horse power motor (not shown). It is preferred to use two (2) chopper motors (not shown; one for each chopper 60), one main drive motor, two plows 50 in chamber 30 having a usable volume capacity of from about 200 to about 400 liters. Such a chamber should be large enough to accommodate a dry reactant batch size from about 20 kg to about 600 kg, preferably 50 kg, 100 kg or 150 kg.

Figure 2:
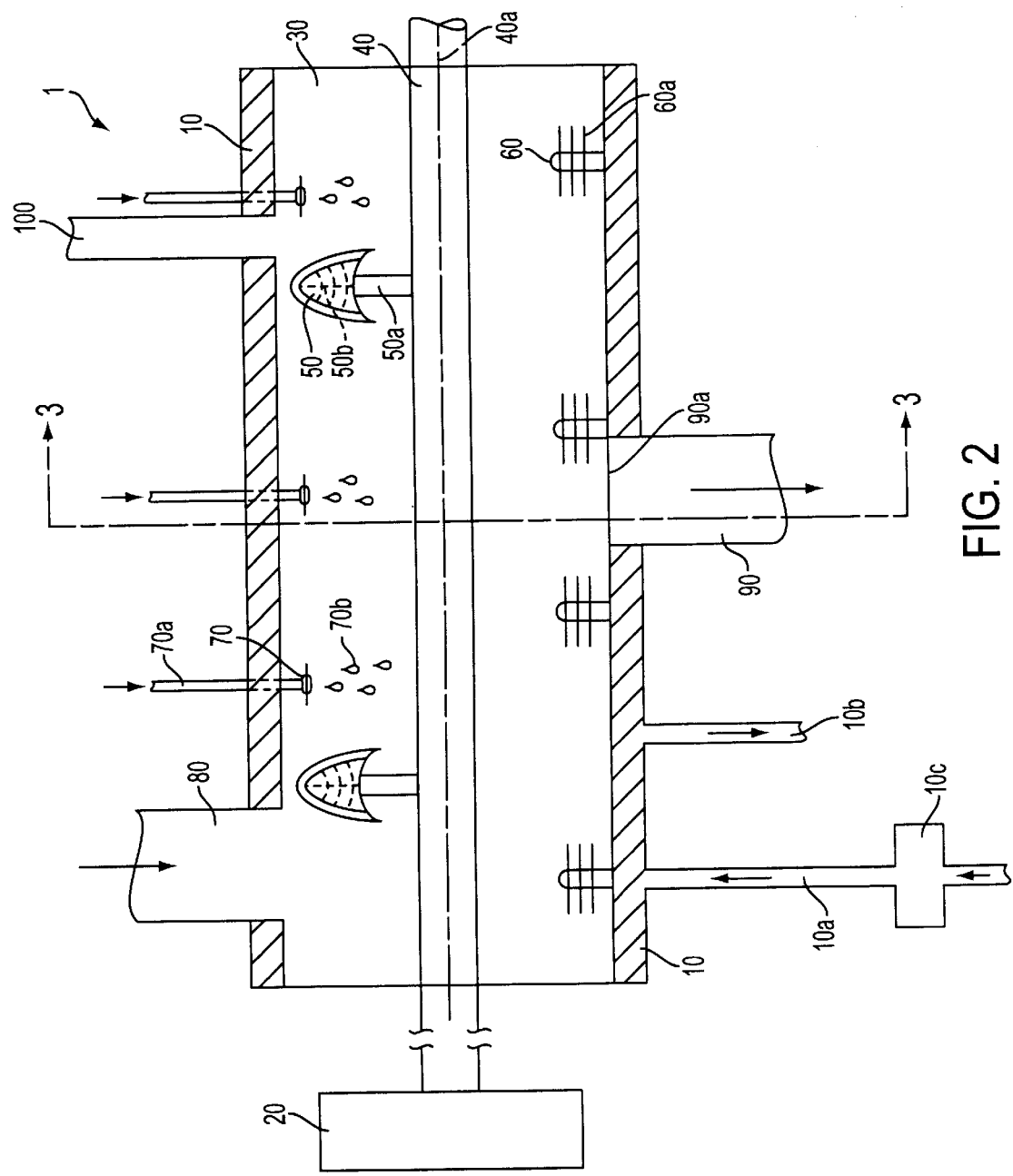
FIG. 2 is a schematic diagram of an exemplary set-up of a reactor vessel (e.g., a reactor/mixer vessel) and its components suitable for preparing mineral, food or pharmaceutical grade salt products in accordance with the present inventive process (e.g., such as a Littleford reactor).
Figure 3:
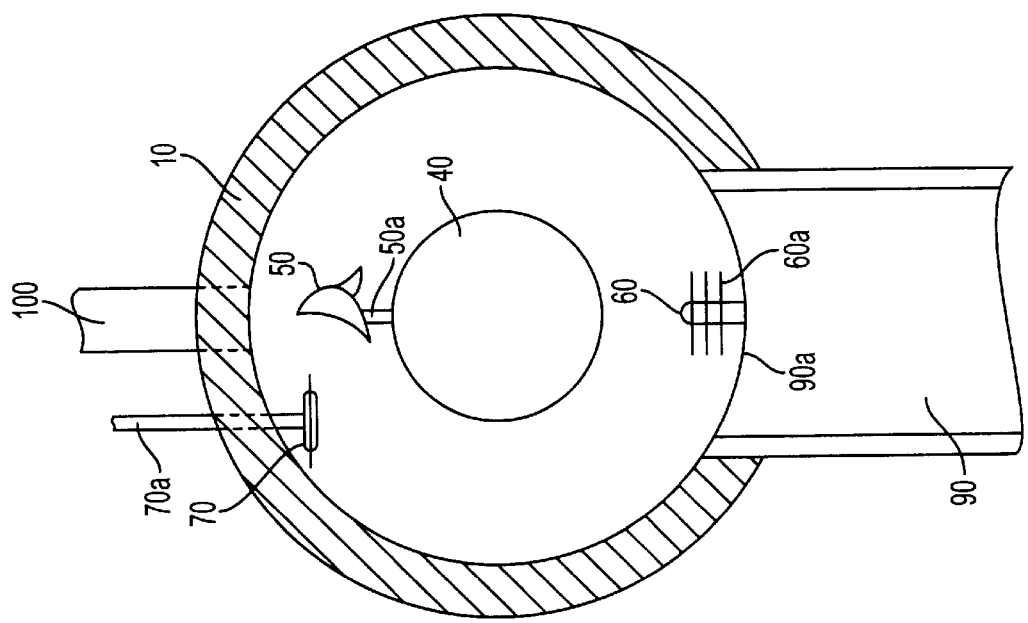
FIG. 3 is a cross-sectional view of the exemplary reactor vessel of FIG. 2.

Typically, once reactants are loaded into chamber 30, the main drive motor is turned on to rotate shaft 40 and plows 50. Additionally, choppers 60 are turned on and heating is provided via steam jacket 10. When the temperature of the so-loaded reactants reaches the first set point temperature, a fluid (e.g., preferably water or an aqueous solution) is introduced into chamber 30 via one or more fluid inlet ports 70 connected to a fluid or water supply chamber (not shown) via supply line(s) 70a. While, three ports 70 are shown in FIG. 2, typically one or more ports 70 may be provided sufficient to introduce water (or other suitable fluid) at a rate of about 1 U.S. gallon/minute into chamber 30. Preferably, the water is at a temperature from about 55° F. to about 90° F., preferably from about 60° F. to about 70° F.

While the fluid herein is described in terms of water, any equivalent fluid may be used that initiates reaction between all or substantially all of the reactants. Venting of gases and $H_2O$ vapor is accomplished through exemplary vent 100 to provide the desired mineral, food or pharmaceutical grade salt product. Instead of vent 100, any equivalent venting means may be provided. Such venting means include vent holes, vent slats, vent apertures or the like. Exemplary mineral, food or pharmaceutical grade salt products that may be made according to the present inventive process are listed in Table I below. The amount of water introduced into chamber 30 is that amount sufficient to just form a "wet powder" of all the reactants previously introduced into chamber 30. For a 100 kg batch of dry granular reactants, typically water from about 1 to about 6 U.S. gallons is introduced via ports 70. Preferably, the water is introduced into chamber 30 with the plows and/or choppers properly rotating.

Inlet ports 70 may be spray nozzles, atomizers, tubes or any equivalent structure sufficient to introduce the needed amount of water at the required rate to form a "wet powder" of all or substantially all of the reactants in chamber 30. Preferably, the amount of water added to the reactants is that amount just sufficient (a minimum amount of water) to form a "wet powder" of all or substantially all of the reactants in chamber 30. The term "wet powder" refers to all or substantially all of the reactants in a wetted or moist form so wetted with a minimum amount of water. For example, the so-specified amount of water is from about 1 to about 20 U.S. gallons, preferably from about 1 to about 6 U.S. gallons, for a reactant batch size of about 100 kg. However, more or less water may be needed to make various mineral, food or pharmaceutical grade salt products as exemplified in Table I below. Of course, the amount of water added may be adjusted upwards or downwards as the batch size is increased or decreased, respectively. For hygroscopic combinations of reactants, less water than from about 1 to about 6 U.S. gallons may be required for a 100 kg batch of dry or essentially dry reactants.

It should be noted that upon addition of the water to chamber 30, the temperature inside the chamber typically dips below the first set point temperature (unless of course the reaction between the reactants is sufficiently exothermic). Typically, after introduction of the required amount of water, the plows and/or choppers continue to be rotated (either continuously or intermittently) until the first set point temperature is established or re-established.

Once the first set point temperature is established in chamber 30, either by increasing or decreasing the heat transfer rate from the steam jacket 10 to chamber 30, the steam jacket thermostat (not shown) is adjusted to heat chamber 30 to a second set point temperature, which preferably is greater than the first set point temperature. Typically, the second set point temperature is from about 190° F. to about 250° F., preferably from about 200° F. to about 249° F., more preferably from about 225° F. to about 248° F., even more preferably from about 230° F. to about 241° F., and most preferably about 240° F. Other exemplary second set point temperatures include 190° F., 195° F., 200° F., 205° F., 210° F., 215° F., 220° F., 225° F., 230° F., 235° F., 240° F. and 250° F. With the second set point temperature being set, the "wet powder" is preferably continuously mixed with one or more plows 50 and/or choppers 60. Adequate heating by the steam jacket 10 is provided to heat the chamber 30 contents to achieve the desired moisture content of the mineral, food or pharmaceutical grade salt product.

It is possible to achieve the desired moisture content before the contents of chamber 30 actually reach the second set point temperature. Accordingly, the term "adjusting the temperature of the reactants to a second set point temperature" means setting the steam jacket thermostat (not shown) to the second set point temperature and heating the contents of chamber 30 until the desired moisture content is reached. Thus, while the steam jacket thermostat (not shown) is set to the second set point temperature, the contents of chamber 30 (though heated to and above the first set point temperature) including the mineral, food or pharmaceutical grade salt product may never actually be heated right up to the second set point temperature because the desired moisture content already has been reached and further heating is unnecessary. Usually, the actual temperature of the chamber 30 contents is typically within about 40° F., 20° F., 10° F., 5° F. or 0° F. (typically lower than the second set point temperature) of the second set point temperature itself.

However, if necessary to obtain the desired moisture level, the contents of chamber 30 may be heated right up to or very nearly the second set point temperature. Most often, however, heating the chamber 30 contents right up to the second set point temperature is not necessary. Preferably, when the chopper motor current draw drops down to about 1–5 amperes, more preferably down to about 1–3 amperes, the chopper motors are shut down and the chopper rotation stopped.

For a 100 kg batch of dry reactants, usually after about 1 hour of heating with the steam jacket thermostat set to the second set point temperature, the "wet powder" is typically converted to a "dry product mix." To determine if the "dry powder mix" has the desired moisture content, the main drive motor 20 is shut down, and samples of the "dry powder mix" are collected to determine their moisture content. Except for when samples are collected, the mixing with plows 50 and/or choppers 60 and heating via the steam jacket 10 are continued until the desired moisture content is achieved. Monitoring of the moisture content is achieved by the above-noted sampling procedure. Preferably, a Mettler Toledo, HR73-P Halogen Moisture Analyzer (made in Switzerland) is used.

Often, when the temperature of the contents of chamber 30 changes more than 1° F./minute for at least 5 minutes, typically the "dry powder mix" within chamber 30 will exhibit a moisture content of less than 4%. Once the desired moisture content is reached, the main drive motor 20 may be shut down. At this point, it is preferred to reduce the second set point temperature to about 70° F. to stop any further steam from flowing through steam jacket 10 allowing the chamber 30 and its contents to cool down to about 140–160° F., preferably down to about 150–160° F., and most preferably down to about 160° F. (assuming the second set point temperature was at or above about 140–160° F.). Optionally, cooling water may be transported through steam jacket 10 to facilitate the cooling of chamber 30 contents. Upon sufficient cooling of chamber 30 and its contents, door 90a is opened and, with the plows 50 turning via shaft 40 attached to motor 20, the contents of chamber 30 are preferably dropped into plastic (or other inert material suitable to collect the contents of chamber 30) lined containers.

The above-noted process may be repeated with the next batch of reactants after sufficient cleaning of the reactor vessel and/or nozzles (if clogged).

By the present inventive process, rates of formation of the mineral, food or pharmaceutical grade salt product may be on the order of from about 24 pounds to about 1000 pounds of product per hour. Typically, rates of formation of about 240 pounds per hour or greater are preferred. Exemplary rates of formation are indicated in the examples below.

Figure 1B:
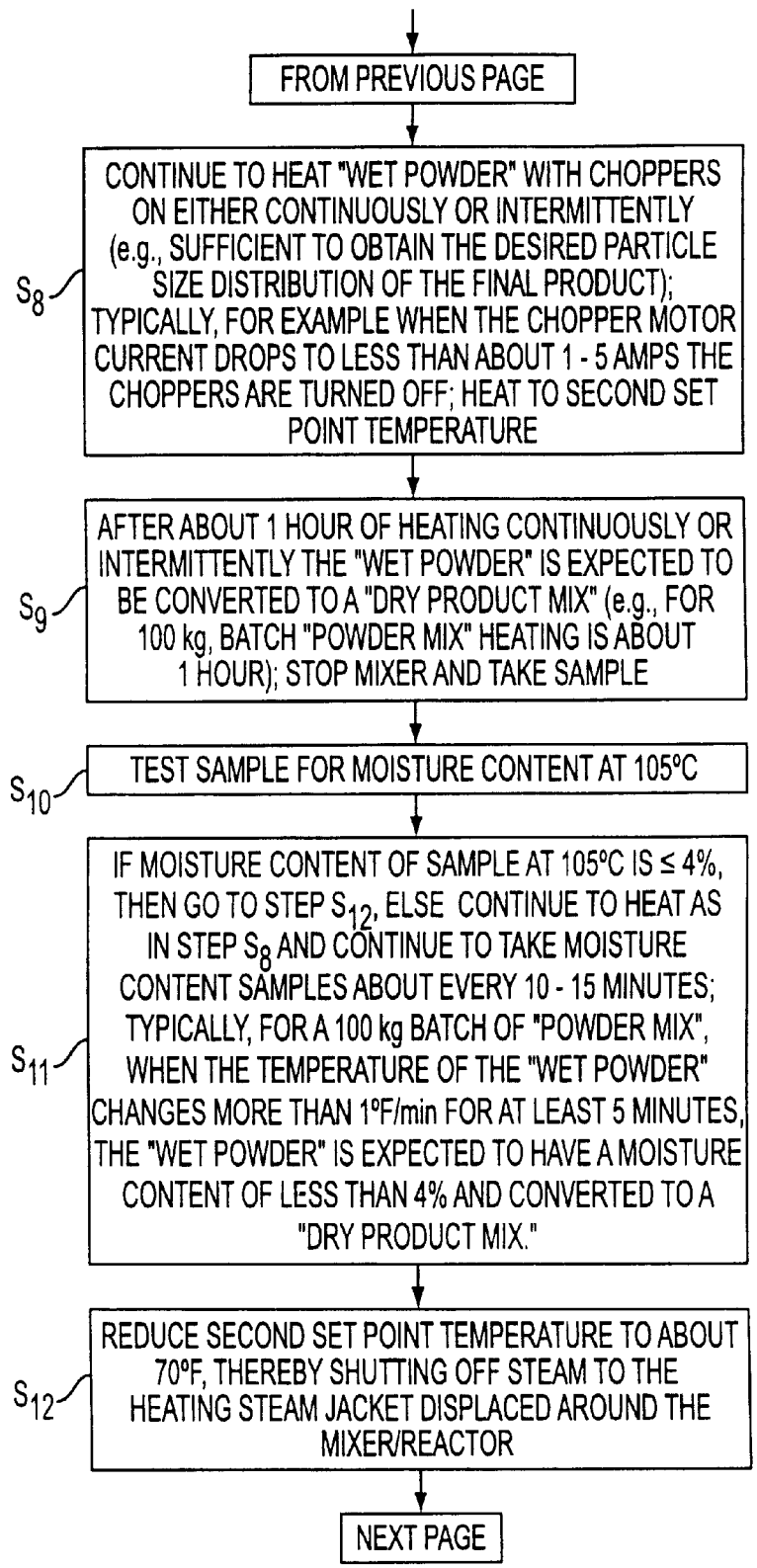
Figure 1C:
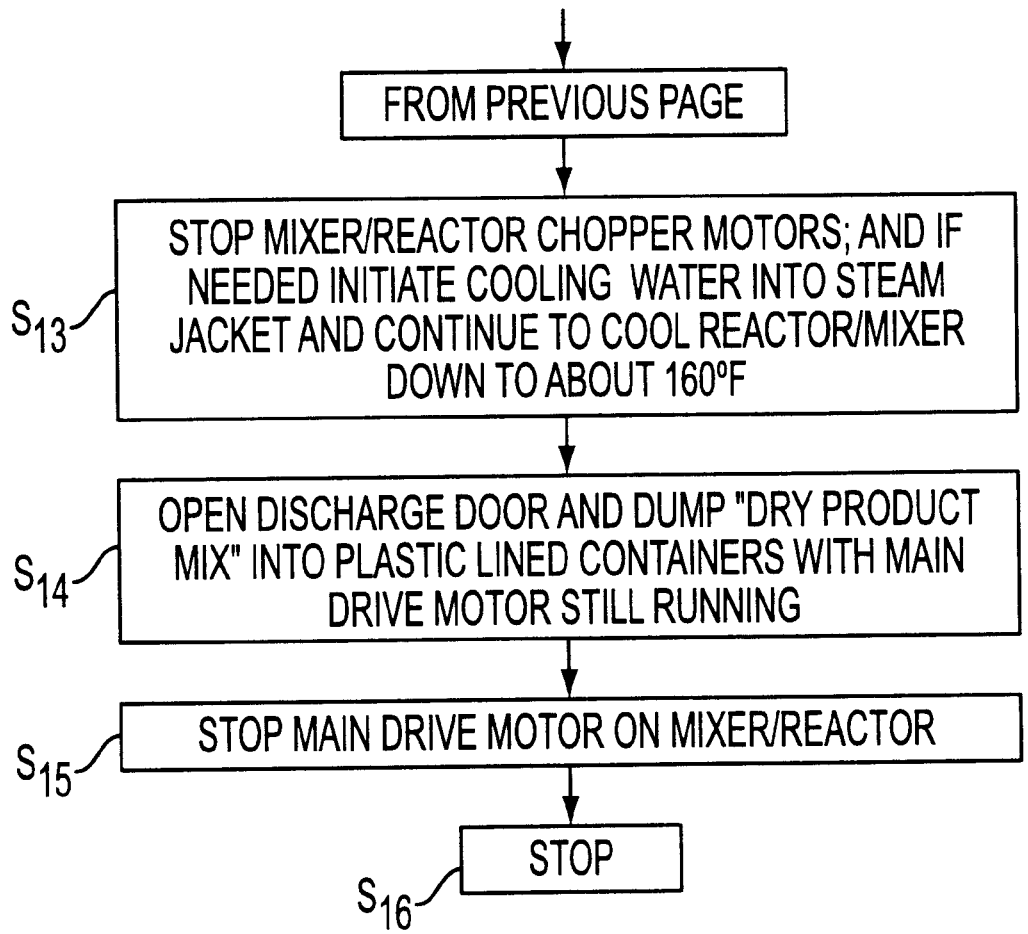
Figure 4:
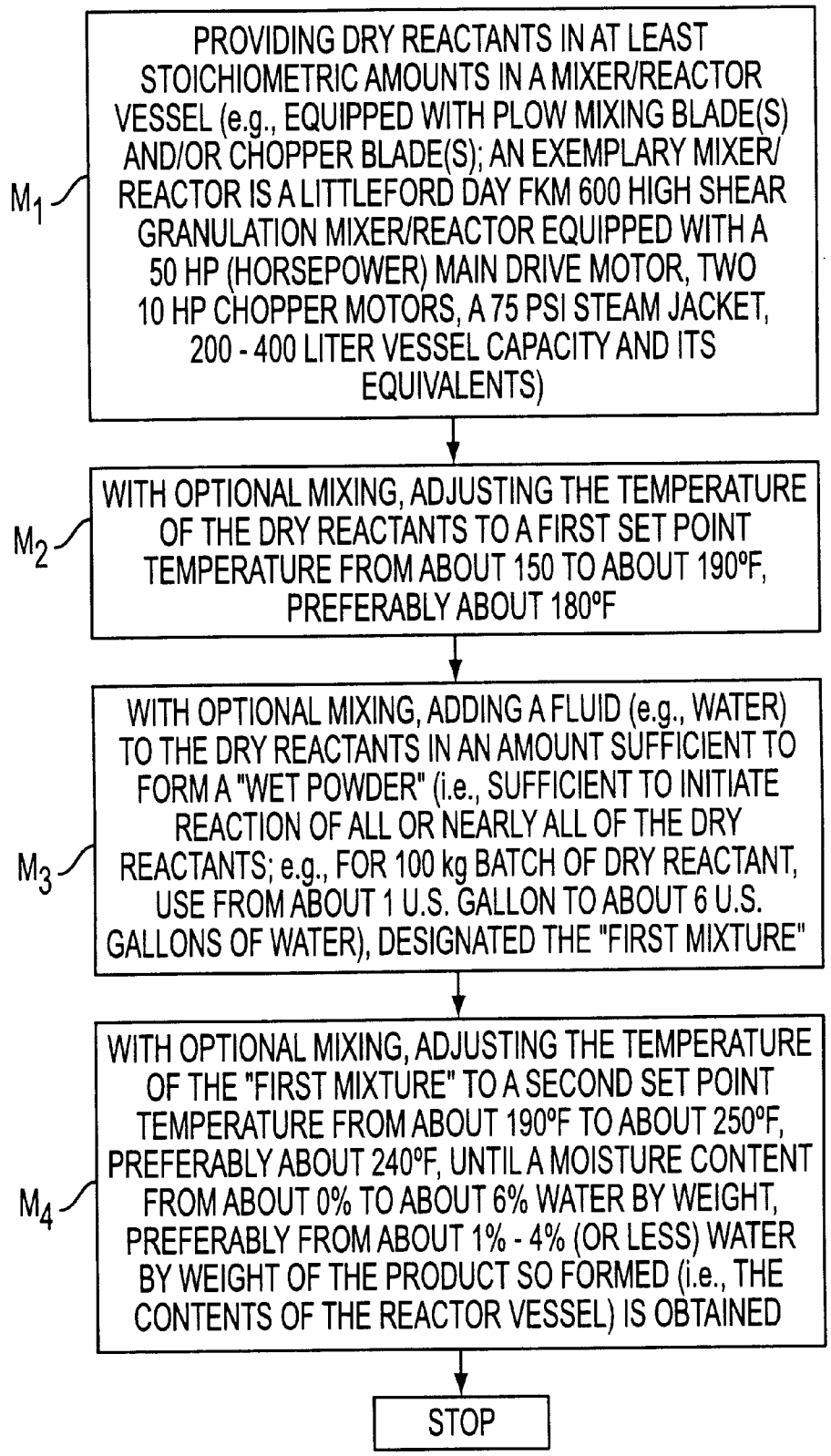
FIG. 4 represents a flow-chart of another exemplary process in accordance with the present invention outlining various process steps.

FIG. 4 is a flow-chart similar to that of FIGS. 1a–1c. Since FIG. 4 is self-explanatory, its steps are not further described herein.

Having described the present invention, the following examples are provided to illustrate the same. It is understood that the Examples are preferred embodiments of the claimed invention and that modifications and variations thereof are well within the scope of the appended claims.

EXAMPLE 1

Exemplary Process Description

1. Dry reactants weighed out and loaded into mixer.
2. Initiate mixing of dry reactants using only the main drive motor.
3. Monitor time, motor amps (main and chopper), material temperature (70–230° F.), set point temperature, mixer internal pressure (0–10" water), water flow and total water used.
4. Enter the First Set Point reactant temperature of 180° F. into set point controller controlling the valve that allows the steam into the steam jacket (e.g. 75 psi steam jacket) on the mixer.
5. Continue to mix dry reactants until they reach the First Set Point temperature.
6. Turn on the chopper motors (e.g., or 500–4000 rpm, preferably 3600 rpm, 10 HP motor).
7. Initiate reaction by adding water at a rate of approx. 1 U.S. gal/minute until the required amount of water has been added.
8. When the chopper motor current drops to less than 1–3 amps, indicating that the choppers are no longer required, turn off the choppers. Reactivate choppers, as necessary to achieve desired particle size distribution.
9. After reactants are established or re-established at the First Set Point temperature, change the First Set Point temperature to a higher Second Set Point temperature of 230° F. to initiate drying cycle.
10. At approx. 1 hour the mixer is stopped and a sample of the material is removed and tested for moisture content. (The temperature of the material will be approx. 204° F.)

11. Re-start the mixer and continue to dry the material to less than 4% moisture content when tested on the moisture checker (Mettler Toledo, HR73-P Hologen Moisture Analyzer manufactured in Switzerland) at 105° C.
12. Take a material sample every 10–15 minutes for the purpose of determining the moisture content. (We have found from experience that by observing the rate of change in material temperature and noting that when the material temperature changes more than 1° F./minute for at least 5 minutes we can be assured that the material has reached a moisture content that is less than 4%.)
13. When the material has been dried to less than or equal to the required moisture content, the Second Set Point temperature should be set to 70° F., thereby shutting off the steam to the steam jacket.
14. If needed to cool reactor vessel, initiate cooling water into the steam jacket and continue to cool the vessel down to 160° F.
15. Open the discharge door and dump material into barrels lined with plastic bags. (The mixer (main drive motor) is preferably running while this is happening.)
16. Stop mixer.
17. Open mixer loading door and check to see that the water injection nozzles are not plugged by momentarily opening water injection valve. Clean nozzle(s) as required.
18. Repeat steps 1–18 above for next batch.

In accordance with the present invention, the following exemplary products listed in Table I below may be made.

TABLE I

| | PRODUCT INFORMATION | | Raw | | | LITTLEFORD PARAMETERS | |
|---|---|---|---|---|---|---|---|
| Item | Product | Code | Material | Amount | | Batch Size (Kg) | Time, hr (best guess/ Littleford) |
| 1 | Ca Citrate 21% | 91018210 | Water | 8.75 | gal | 100 | 1.5 |
| | | | Calcium Carbonate | 60.0 | kg | | |
| | | | Citric Acid | 68.1 | kg | | |
| 2 | Mg HVP 20% | 93005200 | Water | 4 | gal | 100 | 1.0 |
| | | | Alcalase | .083 | kg | | |
| | | | Aspartic Acid | 1.666 | kg | | |
| | | | Rice Protein | 40.0 | kg | | |
| | | | Citric Acid | 15.133 | kg | | |
| | | | MgO (powder) | 37.7 | kg | | |
| 3 | Ca Amino-min | 91006200 | Water | 4.5 | gal | 100 | 1.5 |
| | | | Aspartic Acid | 2.17 | kg | | |
| | | | Ca Carbonate | 55.26 | kg | | |
| | | | Rice Flour | 37.0 | kg | | |
| | | | Citric Acid | 17.39 | kg | | |
| 4 | Mg Citrate 16% | 93018160 | Water | 12 | gal | 100 | (2.5) |
| | | | Citric Acid | 68.1 | kg | | |
| | | | MgO (powder) | 29.0 | kg | | |
| 5 | Mg Aspartate 20% | 93402200 | Water | 4–8 | gal | 100 | (2) |
| | | | Aspartic Acid | 50.0 | kg | | |
| | | | MgO (powder) | 35.6 | kg | | |
| 6 | Mg Amino-min 20% | 93006200 | Water | 5 | gal | 100 | 1.25 |
| | | | Aspartic Acid | 2.17 | kg | | |
| | | | Rice Flour | 34.78 | kg | | |
| | | | Citric Acid | 17.39 | kg | | |
| | | | MgO | 35.7 | kg | | |

TABLE I-continued

| | PRODUCT INFORMATION | | Raw | | | LITTLEFORD PARAMETERS | |
|---|---|---|---|---|---|---|---|
| Item | Product | Code | Material | Amount | | Batch Size (Kg) | Time, hr (best guess/ Littleford) |
| | | | (powder) | | | | |
| 7 | K Aspartate 22.7% | 95042227 | Water | 5 | gal | 100 | 2 |
| | | | K Carbonate | 48.4 | kg | | |
| | | | Aspartic Acid | 72.0 | kg | | |
| | | | MgO (powder) | 10.4 | kg | | |
| 8 | Mg Malate 15.2% | 93054152 | Water | 19.62 | gal | 100 | 3 |
| | | | Malic Acid | 62.5 | kg | | |
| | | | MgO (powder) | 29.434 | kg | | |
| 9 | Ca Malate 23% | 91054230 | Water | 8.0 | gal | 100 | 3 |
| | | | Malic Acid | 77.0 | kg | | |
| | | | Calcium Carbonate | 60.0 | kg | | |
| 10 | Zn Citrate 30% | 97518300 | Water | 16.666 | gal | 100 | 2.25 |
| | | | ZnO | 42.941 | kg | | |
| | | | Citric Acid | 65.441 | kg | | |
| 11 | Mg Krebs 16% | 93039160 | Water | 5–20 | gal | 100 | (4) |
| | | | AKG | .442 | kg | | |
| | | | Fumaric Acid | 17.714 | kg | | |
| | | | Malic Acid | 17.714 | kg | | |
| | | | Succinic Acid | 1.771 | kg | | |
| | | | Citric Acid | 31.886 | kg | | |
| | | | MgO (powder) | 32.329 | kg | | |
| 12 | Mg Aspartate 8.4% | 93042084 | Water | 4–10 | gal | 100 | (3) |
| | | | Aspartic Acid | 82.8 | kg | | |
| | | | MgO (powder) | 16.2 | kg | | |
| 13 | Ca Gluconate 9% | 91027090 | Water | 3–6 | gal | 100 | (2) |
| | | | Calcium Carbonate | 26.1 | kg | | |
| | | | GDL | 81.27 | kg | | |
| 14 | Zn Amino-min 20% | 97506200 | Water | 5–10 | gal | 100 | (2.25) |
| | | | Aspartic Acid | 2.17 | kg | | |
| | | | ZnO | 25.0 | kg | | |
| | | | Rice Flour | 58.0 | kg | | |
| | | | Citric Acid | 17.39 | kg | | |
| 15 | Ca Krebs 22% | 91039220 | Water | 4–10 | gal | 100 | (2.5) |
| | | | AKG | .12 | kg | | |
| | | | Calcium Carbonate | 60.0 | kg | | |
| | | | Fumaric Acid | 11.2 | kg | | |
| | | | Malic Acid | 10.0 | kg | | |
| | | | Succinic Acid | 4.0 | kg | | |
| | | | Citric Acid | 51.0 | kg | | |
| 16 | Ca Lactate 18% | 91048180 | Water | 4–10 | gal | 100 | (2.5) |
| | | | Ca Carb./low Pb | 48.0 | kg | | |
| | | | Lactic Acid | 94.0 | kg | | |
| 17 | Mg Gluconate 5% | 93027050 | Water | 4–10 | gal | 100 | (2.5) |
| | | | GDL | 96.9 | kg | | |
| | | | Mg Carbonate | 23.37 | kg | | |
| 18 | Mn Citrate 28% | 93518280 | Water | 4–15 | gal | 100 | (3.5) |
| | | | Mn Carbonate | 67.44 | kg | | |
| | | | Citric Acid | 50.0 | kg | | |
| 19 | Se Amino-min 1% | 95506010 | Water | 5–15 | gal | 100 | (3.5) |
| | | | Aspartic Acid | 5.0 | kg | | |
| | | | Sodium | 2.8 | kg | | |

TABLE I-continued

LITTLEFORD PARAMETERS

| Item | Product | Code | Raw Material | Amount | Batch Size (Kg) | Time, hr (best guess/Littleford) |
|---|---|---|---|---|---|---|
|  |  |  | Selenite Rice Flour | 75.0 kg |  |  |
|  |  |  | Citric Acid | 10.0 kg |  |  |
|  |  |  | MgO (powder) | 10.0 kg |  |  |
| 20 | Ca Orotate 11.4% | 91058114 | Water | 4–15 gal | 100 | (3.5) |
|  |  |  | Ca Carbonate | 29.23 kg |  |  |
|  |  |  | Orotic Acid | 88.6 kg |  |  |
| 21 | Ca Mg Aminomin 24/12 | 10227 | Water | 8 gal | 100 | 1.25 |
|  |  |  | Aspartic Acid | 3.044 kg |  |  |
|  |  |  | Ca Carbonate | 37.594 kg |  |  |
|  |  |  | Lime (CaOH$_2$) | 20.443 kg |  |  |
|  |  |  | Rice Protein | 1.044 kg |  |  |
|  |  |  | Rice Flour | 5.158 kg |  |  |
|  |  |  | Citric Acid | 4.278 kg |  |  |
|  |  |  | MgO (powder) | 23.689 kg |  |  |
| 22 | Cu Gluconate 13% | 92027130 | Water | 4–8 gal | 100 | (2.5) |
|  |  |  | Cu Carbonate | 30.0 kg |  |  |
|  |  |  | GDL | 90.0 kg |  |  |
| 23 | K Succinate 33% | 95075330 | Water | 2–8 gal | 100 | (2) |
|  |  |  | K Carbonate | 58.62 kg |  |  |
|  |  |  | Succinic Acid | 50.09 kg |  |  |
| 24 | V Krebs 0.5% | 97039005 | Water | 3–11 gal | 100 | (3) |
|  |  |  | AKG | .03 kg |  |  |
|  |  |  | Fumaric Acid | .49 kg |  |  |
|  |  |  | Malic Acid | .49 kg |  |  |
|  |  |  | Succinic Acid | .03 kg |  |  |
|  |  |  | Vanadium Pentoxide | 1.05 kg |  |  |
|  |  |  | Citric Acid | .99 kg |  |  |
|  |  |  | DCP-Calcium (Anhydride) | 97.99 kg |  |  |
| 25 | Mo Krebs 0.5% | 94039005 | Water | 5 gal | 100 | (1.5) |
|  |  |  | AKG | .03 kg |  |  |
|  |  |  | Fumaric Acid | .49 kg |  |  |
|  |  |  | Malic Acid | .49 kg |  |  |
|  |  |  | Sodium Molydate | 1.538 kg |  |  |
|  |  |  | Succinic Acid | .03 kg |  |  |
|  |  |  | Citric Acid | .99 kg |  |  |
|  |  |  | DCP-Calcium (Anhydride) | 98 kg |  |  |
| 26 | Ca Asporotate 20% | 102200 | Water | 3–9 gal | 100 | (3) |
|  |  |  | Aspartic Acid | 56.908 kg |  |  |
|  |  |  | Ca Carbonate | 40.908 kg |  |  |
|  |  |  | Lime (CaOH$_2$) | 18.0 kg |  |  |
|  |  |  | Whey Concentrate | 2.726 kg |  |  |
|  |  |  | Citric Acid | 4.545 kg |  |  |
| 27 | Mg Asporotate 20% | 102250 | Water | 4–15 gal | 100 | (3.5) |
|  |  |  | Aspartic Acid | 42.68 kg |  |  |
|  |  |  | Whey Concentrate | 2.328 kg |  |  |
|  |  |  | Citric Acid | 3.88 kg |  |  |
|  |  |  | MgO (powder) | 41.128 kg |  |  |
| 28 | Mg Succinate 17% | 93075170 | Water | 4–15 gal | 100 | (3.5) |
|  |  |  | Succinic Acid | 44.9 kg |  |  |
|  |  |  | Citric Acid | 14.012 kg |  |  |
|  |  |  | MgO (powder) | 30.9 kg |  |  |
| 29 | Mn L-ASP 17% | 93542170 | Water | 4–15 gal | 100 | (3.5) |
|  |  |  | Aspartic Acid | 82.0 kg |  |  |
|  |  |  | Mn Carbonate | 41.86 kg |  |  |

AKG = Alphaketoglutaric
GDL = Glucono Delta Lactone
Ca Carb./low Pb = Calcium Carbonate/Low Lead
DCP Calcium = Dicalcium Phosphate Calcium

EXAMPLE 2

Another exemplary procedure in accordance with the present invention is outlined below reciting various stages.

Advantageously, exemplary stages 1–5 are completed in a single reactor vessel h reduces the associated costs, reduces the processing time to ⅓–⅒ (for the entire process from start to finish) of that normally associated with conventional processes for making the same size product batch with equal or increased yield and/or purity level.

Stage 1—weighing Stage

The reactants are weighed out in the quantities listed in Table I. Preferably, all the reactants are provided in a dry powdery form, although a slight moisture content may be tolerated (e.g., up to about 11–15%).

Stage 2—powder Mix Stage

The appropriate quantities of reactants are placed into the reactor vessel cavity. The temperature of the reactor vessel is adjusted to the first set point temperature. This first set point temperature is preferably 185±10° F. The reactants are heated and mixed until their temperature reaches the first set point temperature to yield a "powder mix." Hence, this stage is called the "powder mix" stage.

Stage 3—wet Powder Mix Stage

To the "powder mix" of stage 2 adjusted to the first set point temperature, a fluid (e.g., preferably, water or an aqueous solution) is added at a rate of less than or equal to about 1 U.S. gallon per minute in an amount just sufficient to form a "wet powder mix" of all of the "powder mix" of stage 2 above. Preferably, the fluid is water and, more preferably, the fluid is water at a fluid temperature from about 55° F. to about 90° F. The combination of the "powder mix" and the "fluid" yields a "wet powder mix." Hence, this stage is called the "wet powder mix" stage.

Upon addition of the fluid, the temperature of the "powder mix" when combined with the "fluid" typically dips below the first set point temperature, unless there is a sufficiently exothermic reaction to maintain or increase the temperature at or above the first set point temperature. The combined "fluid" and "powder mix" are mixed and heated, as necessary, until the temperature thereof is established or re-established at the first set point temperature.

Stage 4—drying Stage

Next, a new set point temperature is established, designated as the second set point temperature. The second set point temperature is typically greater than the first set point temperature. Preferably, the second set point temperature is about 240±10° F. The "wet powder mix" from stage 3 is mixed and heated (e.g., preferably heated not to exceed the second set point temperature) until its desired moisture content is reached, e.g., less than about 4% moisture content. The resulting product is called the "dry product mix." Caution must be undertaken not to overuse the choppers. The preferred particle size distribution of the "dry product mix" so formed should be from about 140# mesh to about 20# mesh. Overuse of the choppers will reduce the particle size undesirably below 140# mesh and produce an undesirably fine power and/or low product density.

The choppers need to be used sparingly so that an excess of "powder" is not formed. The desired product should mostly have a granular texture as opposed to a powder texture. The benefit of forming a granular material as opposed to a powder material is that the granular material can be later ground to the desired mesh size, as necessary. Whereas, with a powder material it is difficult to achieve small mesh # sizes (larger particles) because the powder cannot be easily reformulated into larger granules. Moisture samples may be taken every 15 minutes or sooner or until the final moisture content satisfies the product specification.

Typically, the final product moisture content is from about 1% to about 6% for products such as calcium citrate 21%. The desired moisture content is set to that which satisfies the product specification. Once the desired moisture level has been achieved, the heat source is turned off and the product material cooled, preferably in the reactor vessel for a typical start to finish processing time from about ½–2 hours (excluding any time during which the process has been interrupted or sitting idle for any variety of reasons including an attempt to design around the claimed invention) for batch sizes comparable to those listed in Table I. It is noted, however, as batch sizes are increased or decreased, the total processing time (from start to finish) will be proportionately adjusted upwards or downwards, respectively.

It is noted that a substantial advantage of the present process is the ability to complete substantially all of the necessary drying in the reactor vessel itself so that separate drying chambers (and the disadvantages associated therewith) are unnecessary.

The so-formed product is converted from its "wet powder mix" formation to a "granular" formation called the "dry product mix." Hence, this stage is designated as the "dry powder mix" stage or the "drying" stage.

Stage 5—grinding Stage (Optional)

At this stage, the particle size distribution and the product density are measured. If any further grinding is necessary to achieve the desired particle size distribution, such grinding is accomplished by methods known to those skilled in the art.

For measurement of the particle size distribution, the final granular product is placed in a "Rotap," or equivalent machine which is designed for the purpose of establishing the particle size distribution. Additionally, the bulk density is measured using a "Tap Density Machine" or its equivalent. The resulting particle size distribution and tap density are compared to the product specification to determine if any further grinding is necessary. Grinding is carried out as necessary by methods known to those skilled in the art. As noted, the grinding stage is optional. This stage is designated as the "grinding" stage.

EXAMPLE 3

Preparation of Ca-citrate 21%

| Materials: | Water | 2.2 gallons |
|---|---|---|
| | Calcium Carbonate | 12.2 kg |
| | Citric Acid | 13.5 kg |

A Littleford reactor vessel (Littleford Day FKM 130 High Shear Granulation Mixer/Reactor equipped with a main drive motor, one chopper motor, and 75 psi steam jacket) was set to be heated to a first set point temperature of about 180±10° F. The powders of dry materials (calcium carbonate and citric acid) were added into the reactor vessel and blended (with the plows) until the temperature of the blended materials reached about 180° F. At that temperature, the choppers were turned on (3600 rpm) and water was added to the blended powder materials. Addition of the water lowered the temperature of the reactor vessel and its contents to about 136° F. Upon addition of the water, the reaction mixture was transformed from a liquid consistency through a doughy consistency to a powder and bead consistency to yield a "wet powder mix."

The second set point temperature was set to 190° F. after the reactor had stabilized at the first set point temperature. With mixing, the "wet powder mix" containing water and the previously dry reactant materials were heated to the second set point temperature of 190±5° F. The reaction mixture of water, calcium carbonate and citric acid reached a high temperature of 192° F. Once the second set point temperature was reached, product sample moisture measurements were taken. When the moisture of the product salt reached less than or equal to 6% water when tested at 105° C., then the Ca-citrate 21% product salt was removed from the reactor vessel after cooling in accordance with steps $S_{12}$–$S_{14}$ of FIGS. 1a–1c. The above-noted product had a density of 1.08 g/ml and a particle size distribution as follows:

20 mesh: 59.65% by weight
60 mesh: 34.50% by weight
140 mesh: 3.80% by weight
pan: 1.43% by weight
TOTAL: 99.38% by weight.

Sample product moisture content was measured at 15–20 minute intervals throughout the above-noted process steps. The product moisture data was as follows:

Sample #1: 28.6% by weight water at 105° C.
Sample #2: 21.4% by weight water at 105° C.
Sample #3: 14.5% by weight water at 105° C.
Sample #4: 10.5% by weight water at 105° C.
Sample #5: 6.3% by weight water at 105° C.
Sample #6: 3.9% by weight water at 105° C.

The product yield for the above-described procedure of Example 3 was 44 pounds of Ca-citrate 21% prepared in 2.25 hours for a rate of formation of 19.55 pounds/hour.

EXAMPLE 4
Preparation of Ca-citrate 21%

| Materials: | Water | 3.3 gallons |
| --- | --- | --- |
| | Calcium Carbonate | 18.30 kg |
| | Citric Acid | 20.25 kg |

The same procedure outlined in Example 2 was used except that the addition of the water to the reactor vessel lowered the temperature of the reactor vessel and its contents to about 125° F.

The above-noted product had a density of 0.9934 g/ml and a particle size distribution as follows:

20 mesh: 18.20% by weight
60 mesh: 60.69% by weight
140 mesh: 17.10% by weight
pan: 3.99% by weight
TOTAL: 99.98% by weight.

Sample product moisture content was measured at 15–20 minute intervals throughout the above-noted process steps. The product moisture data was as follows:

Sample #1: 27.6% by weight water at 105° C.
Sample #2: 22.5% by weight water at 105° C.
Sample #3: 18.5% by weight water at 105° C.
Sample #4: 12.4% by weight water at 105° C.
Sample #5: 8.6% by weight water at 105° C.
Sample #6: 4.7% by weight water at 105° C.

The product yield for the above-described procedure of Example 4 was 66 pounds of Cacitrate 21% prepared in 2.42 hours for a rate of formation of 29.33 pounds/hour.

EXAMPLE 5
Preparation of Ca-citrate 21%—Littleford Reactor Vessel

| Materials: | Water | 12.0 gallons |
| --- | --- | --- |
| | Calcium Carbonate | 15.18 kg |
| | Citric Acid | 20.2 kg |

The same procedure outlined in Example 3 was used except that the water was added when the first set point temperature of 170° F. was reached and addition of the water lowered the temperature of the reactor vessel and its contents to about 108° F.. Also, the second set point was set to 190° F. With mixing, the water and the previously dry materials were heated to the second set point temperature of 190±5° F. The reaction mixture of water, calcium carbonate and citric acid reached a high temperature of 20°° F.

Upon addition of the water, the reaction mixture was transformed from a liquid consistency through a paste consistency, a doughy consistency, a beads consistency, to a powder and beads consistency. When the beads consistency was achieved, sample moisture measurements were taken.

The above-noted product had a density of 0.8536 g/ml and a particle size distribution as follows:

20 mesh: 74.19% by weight
60 mesh: 21.95% by weight
140 mesh: 3.09% by weight
pan: 0.77% by weight
TOTAL: 100.00% by weight.

Sample product moisture content was measured at 15–20 minute intervals throughout the above-noted process steps. The product moisture data was as follows:

Sample #1: 30.5% by weight water at 105° C.
Sample #2: 26.5% by weight water at 105° C.
Sample #3: 16.9% by weight water at 105° C.
Sample #4: 13.7% by weight water at 105° C.
Sample #5: 6.6% by weight water at 105° C.
Sample #6: 5.1% by weight water at 105° C.

The product yield for the above-described procedure of Example 5 was 66 pounds of Ca-citrate 21% prepared in 3.83 hours for a rate of formation of 17.23 pounds/hour.

EXAMPLE 6
Various Products

Additional products were made in accordance with the procedures outlined in the above-noted Examples. Details regarding these various products are noted below.

| Batch No. (Lot. No.) | Product Made | Rate of Formation (lb/hr) |
| --- | --- | --- |
| 1 (120895) | Mg-L-Asp 20% | 14.7 |
| 2 (120895-2) | Mg-L-Asp 20% | 17.6 |
| 1 (120894) | Mg-citrate 16% | 22 |
| 5 (120893) | Ca-Mg-Aminomin-24-12.5% | 16 |

EXAMPLE 7
Mg-HVP Aminomin 20%—Batch No. 26089 (3–4)

Additional product was made in accordance with the procedures outlined in the above-noted Examples. Details and observations are noted below.

| Batch No. (Lot. No.) | Product Made | Rate of Formation (lb/hr) |
| --- | --- | --- |
| 3–4 (26089) | Mg-HVP-Aminomin 20% | 66 |

The moisture data collected was as follows:

Sample #1: 32.5% by weight water at 105° C. at 33 minutes from start
Sample #2: 22.5% by weight water at 105° C. at 55 minutes from start
Sample #3: 18.2% by weight water at 105° C. at 1 hour 5 minutes from start
Sample #4: 13.8% by weight water at 105° C. at 1 hour 40 minutes from start
Sample #5: 11.3% by weight water at 105° C. at 2 hours 5 minutes from start
Sample #6: 10.1% by weight water at 105° C. at 2 hours 30 minutes from start in the reactor vessel.

The particle size distribution data collected was as follows:

20 mesh: 62.67% by weight
60 mesh: 23.43% by weight
140 mesh: 6.66% by weight
pan: 7.23% by weight
TOTAL: 99.99% by weight.

EXAMPLE 8
Ca-AAC 20%

Additional product was made in accordance with the procedures outlined in the above-noted Examples. Details and observations are noted below.

| Batch No. (Lot. No.) | Product Made | Rate of Formation (lb/hr) |
|---|---|---|
| 6 (25089) | Ca-AAC 20% | 22 |

The above-noted product had a density of 1.18 g/ml. The particle size distribution was as follows:
20 mesh: 74.19% by weight
60 mesh: 21.95% by weight
140 mesh: 3.094% by weight
pan: 0.77% by weight
TOTAL: 100.00% by weight.
The product yield for the above-described procedure of Example 8 was 22 pounds of Ca-AAC 20% prepared in 1 hour for a rate of formation of 22 pounds/hour.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A process for forming a mineral, food or pharmaceutical grade salt product, said process comprising the steps of:
   (a) loading or providing reactants in a reactor vessel;
   (b) with optional mixing, adjusting the temperature of the reactants to a first set point temperature in said reactor vessel, wherein the first set point temperature is above about 25° C. when operating said process at about 1 atmosphere pressure;
   (c) with optional mixing, adding a fluid to the reactants of step (b) in an amount sufficient to initiate reaction of all or nearly all of the reactants to form a first mixture; and
   (d) with optional mixing, adjusting the temperature of the first mixture to a second set point temperature, when operating said process at about 1 atmosphere pressure, of at least 190° F. for a time sufficient to evaporate substantially all of the fluid to yield said mineral, food or pharmaceutical grade salt product having a moisture content of less than about 6%, wherein said steps (a)–(d) are completed in said reactor vessel.

2. The process of claim 1, wherein said fluid comprises water.

3. The process of claim 2, wherein said fluid is water and said water is added in said step (c) at a rate of about 1 U.S. gallon/minute.

4. The process of claim 1, wherein said first set point temperature is from about 170° F. to about 190° F.

5. The process of claim 1, wherein said second set point temperature is from about 230° F. to about 250° F.

6. The process of claim 1, wherein said moisture content is less than about 4%.

7. The process of claim 1, wherein said mineral, food or pharmaceutical grade salt product is selected from the group consisting of Ca Citrate 21%, Mg HVP 20%, Ca Aminomin, Mg Citrate 16%, Mg Aspartate 20%, Mg Aminomin 20%, K Aspartate 22.7%, Mg Malate 15.2%, Ca Malate 23%, Zn Citrate 30%, Mg Krebs 16%, Mg Aspartate 8.4%, Ca Gluconate 9%, Zn Aminomin 20%, Ca Krebs 22%, Ca Lactate 18%, Mg Gluconate 5%, Mn Citrate 28%, Se Aminomin 1%, Ca Orotate 11.4%, Ca Mg Aminomin 24/12, Cu Gluconate 13%, K Succinate 33%, V Krebs 0.5%, Mo Krebs 0.5%, Ca Asporotate 20%, Mg Asporotate 20%, Mg Succinate 17%, and Mn L-Asp 17%.

8. The process of claim 7, wherein a processing time from starting step (a) to completing step (d) is from about ½ to about 6 hours for a total weight of said reactants, excluding said fluid provided in any of steps (a)–(d), is about 100 kg.

9. The process of claim 8, wherein said reactor vessel is a Littleford reactor equipped with at least one mixing element, and optionally at least one chopper, at least one heating element, and at least one fluid nozzle.

10. The process of claim 4, wherein said first set point temperature is about 180° F.

11. The process of claim 5, wherein said second set point temperature is about 190° F.

12. The process of claim 1 further comprising heating said powder mix to about 140° F. in said step (a).

13. The process of claim 8, wherein said processing time is from about 1 to about 2 hours.

14. The process of claim 13, wherein said processing time is about 1 hour.

15. The process of claim 1, wherein a total weight of said reactants, excluding said fluid provided in any of steps (a)–(d), is from about 20 kg to about 600 kg.

16. The process of claim 7, wherein a total weight of said reactants, excluding said fluid provided in any of steps (a)–(d), is from about 20 kg to about 600 kg.

17. The process of claim 1, wherein said moisture content is 4% or less.

18. The process of claim 1, wherein said moisture content is from about 1% to about 4%.

19. The process of claim 1, wherein a total weight of all said reactants utilized in steps (a)–(d), excluding said fluid, is from about 20 kg to about 600 kg, wherein a total processing time for completing said steps (a)–(d) is from about 1 to about 2 hours, wherein said fluid is water, wherein said first set point temperature is about 180° F., and wherein said second set point temperature is about 240° F.

20. A process for forming a mineral, food or pharmaceutical grade salt product, said process comprising the steps of:
   (a) loading or providing reactants in a reactor vessel;
   (b) with optional mixing, adjusting a temperature of said powder mix to a first set point temperature in said reactor vessel, wherein said first set point temperature is above about 25° C. when operating said process at about 1 atmosphere pressure;
   (c) with optional mixing, adding a fluid to said powder mix of step (b) in an amount sufficient to form a wet powder mix to initiate reaction of all or substantially all of said reactants;
   (d) with optional mixing, adjusting a temperature of said wet powder mix to a second set point temperature for a time sufficient to dry said wet powder mix to a moisture content from about 1% to about 6%; and
   (e) stopping the heating and optionally stopping the mixing when said moisture content of said mineral, food or pharmaceutical grade salt product is obtained, wherein any said mixing in this step (e) is just sufficient to form granules, and wherein said steps (a)–(e) are carried out in said reactor vessel.

21. The process of claim 20, wherein said first set point temperature is about 180° F. and said second set point temperature is about 240° F.

22. A process for forming a mineral, food or pharmaceutical grade salt product, said process comprising the steps of:
   (a) loading or providing reactants in a reactor vessel;
   (b) with optional mixing, adjusting the temperature of the reactants to a first set point temperature in said reactor vessel, wherein the first set point temperature is from about 150° F. to about 190° F. when operating said process at about 1 atmosphere pressure;

(c) with optional mixing, adding a fluid to the reactants of step (b) in an amount sufficient to initiate reaction of all or nearly all of the reactants to form a first mixture; and (d) with optional mixing, adjusting the temperature of the first mixture to a second set point temperature, when operating said process at about 1 atmosphere pressure, from about 190° F. to about 250° F. for a time sufficient to evaporate substantially all of the fluid to yield said mineral, food or pharmaceutical grade salt product having a moisture content of less than about 6%, wherein said steps (a)–(d) are completed in said reactor vessel.

23. The process of claim 22, wherein said reactants of said step (a) are in a substantially granular form.

24. The process of claim 22, wherein said second set point temperature is greater than said first set point temperature.

25. The process of claim 1, wherein said mineral, food, or pharmaceutical grade salt product is formed by said process at a formation rate of at least about 24 pounds per hour.

26. The process of claim 1, wherein said mineral, food, or pharmaceutical grade salt product is formed by said process at a formation rate of at least about 240 pounds per hour.

27. The process of claim 1, wherein said mineral, food, or pharmaceutical grade salt product is formed by said process at a formation rate of at least about 1000 pounds per hour.

28. A process for forming a mineral, food or pharmaceutical grade salt product, said process comprising the steps of:

(a) loading or providing reactants in a reactor vessel;

(b) with optional mixing, adjusting the temperature of the reactants to a first set point temperature in said reactor vessel, wherein the first set point temperature is about 180° F. when operating said process at about 1 atmosphere pressure;

(c) with optional mixing, adding a fluid to the reactants of step (b) in an amount sufficient to initiate reaction of all or nearly all of the reactants to form a first mixture; and (d) with optional mixing, adjusting the temperature of the first mixture to a second set point temperature, when operating said process at about 1 atmosphere pressure, is about 250° F. for a time sufficient to evaporate substantially all of the fluid to yield said mineral, food or pharmaceutical grade salt product having a moisture content of less than about 6%, wherein said steps (a)–(d) are completed in said reactor vessel.

29. The process of claim 28, wherein said process is operated at about 1 atmosphere pressure.

* * * * *